United States Patent [19]

Kominek et al.

[11] Patent Number: 4,868,122
[45] Date of Patent: Sep. 19, 1989

[54] ARRANGEMENT FOR GROWING PERMANENT FORMS OF MICROORGANISMS

[75] Inventors: Jiri Kominek; Otto Zehentgruber, both of Vienna; Wolfgang Salzbrunn, Wiener Neustadt, all of Austria

[73] Assignee: Vogelbusch Gesellschaft m.b.H., Austria

[21] Appl. No.: 163,609

[22] Filed: Mar. 3, 1988

[30] Foreign Application Priority Data

Mar. 5, 1987 [AT] Austria ................................ 504/87

[51] Int. Cl.⁴ .............................................. C12M 3/02
[52] U.S. Cl. ................................ 435/285; 435/290; 435/310
[58] Field of Search .......................... 435/283–287, 435/289, 290, 291, 310, 311, 316; 422/298, 300, 299, 292

[56] References Cited

U.S. PATENT DOCUMENTS

| 4,225,671 | 9/1980 | Puchinger | 435/287 |
| 4,336,329 | 6/1982 | Hesse et al. | 435/290 |
| 4,753,887 | 6/1988 | Bellare et al. | 435/287 |

Primary Examiner—James C. Yeung
Attorney, Agent, or Firm—Ostrolenk, Faber, Gerb & Soffen

[57] ABSTRACT

There is disclosed an arrangement for growing permanent forms, of microorganism in particular filaments microorganisms. In order to design such an arrangement operationally safe, mobile and compact and with a high adaptability, yet for ensuring sufficiently large production and manipulation surfaces, the arrangement, in which trays for the culture medium are superposed in a box-type container, further includes a feeding chamber and an air-conditioning chamber containing an air-conditioning device united in a common housing. A gas-tightly closeable feed opening is provided in a side wall of the feeding chamber. The air-conditioning device includes sterile filters for sterile-keeping intake air and for filtering offsteaming exhaust air.

11 Claims, 3 Drawing Sheets

FIG. 1
FIG. 6
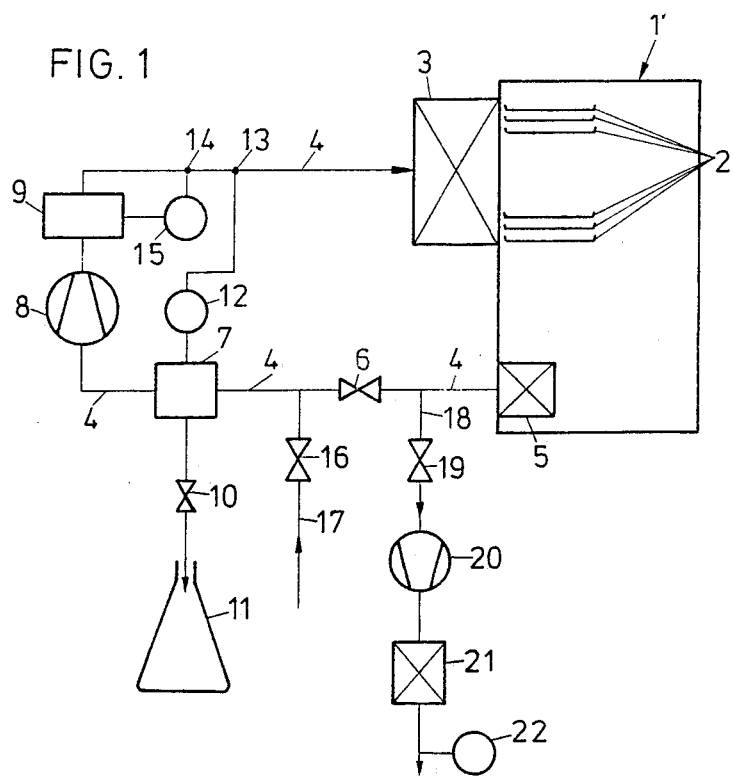
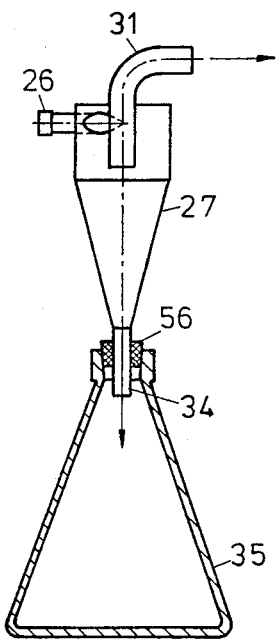

ARRANGEMENT FOR GROWING PERMANENT FORMS OF MICROORGANISMS

BACKGROUND OF THE INVENTION

The invention relates to an arrangement for growing permanent microbial forms, in particular filamentary microorganisms, as well as for harvesting such permanent forms formed on the surface of a culture medium, which arrangement comprises trays for the culture medium superposed in a box-type container.

These microorganisms, called filamentous constitute an expanded system of branched filaments (hyphae), for instance, hyphomycetes and actinomycetes. Such microorganisms frequently form permanent forms projecting out of the culture medium, primarily if they grow on the surface of a liquid or solid culture medium.

Microbial permanent forms, usually called spores, most frequently are used as the starting culture for fermentations. Thus, i.a., *Aspergillus niger* spores are employed for the production of citric acid and spores of the germs Trichoderma are used for the production of cellulase. The use of spores has the advantage that the microorganisms, usually highly efficient production strains, can be stored over long periods of time without loosing their activities.

For use in laboratories and pilot plants, it suffices to produce spores from cultures in larger Petri dishes or trays, in which the microorganism grows on solidified liquid culture by finally forming spores, which are then harvested either in a dried state by sterile brushes, or in a wet state by rinsing with a sterile physiologic saline solution.

However, this relatively simple method has the disadvantage that, for one part, only few spores are obtained on Petri dishes and, for the other part, the humidity of the air within a Petri dish can be controlled to an insufficient extent only.

When culturing on larger trays, on the one hand air-conditioned boxes for temperation and, on the other hand, sterile rooms for harvesting the spores must be available. Besides, the sterile manipulation with such trays mostly is very cumbersome.

The control of the humidity of air is of a particular relevance to the quality and to the yield of spores. For this reason, the following mode of procedure has been chosen so far for the production on an industrial scale:

A, usually displaceable, box is equipped with flat superposed and removable trays. These trays are filled with hot, still liquid, culture medium and the entire box including the trays is sterilized in a large-space sterilizer. Upon cooling and solidification of the culture medium, the box is moved out of the sterilizer and is connected to an air-conditioning plant via sterile filters. Thereupon, incubation with spores is effected via the aerating system, the microorganism is grown under an initially high humidity of the air, and upon the formation of spores, desiccation takes place by means of dry air until the culture medium has become dry and the spores, upon removal of the individual trays, can be harvested in a sterile room. Thus, the prerequisite for an industrial production so far has been the availability of a complex and expensive large-space sterilizer. In addition, sterile rooms had to be available for harvesting. Add to this that the transfer of the trays into the sterile room was quite cumbersome and the harvest of the spores involved considerable periods of time. When growing and harvesting spores of pathogenic microorganisms, the personnel, moreover, was hardly able to be protected from contact with the spores during manipulation.

OBJECT OF THE INVENTION

The invention aims at eliminating the disadvantages and difficulties pointed out and has as its object to provide for an operationally safe and mobile compact arrangement of a high adaptability, which offers sufficiently large production and manipulation surfaces and is not dependent on the existence of a large-space sterilizer as well as of sterile rooms.

SUMMARY OF THE INVENTION

With an arrangement of the initially defined kind, the set object is achieved according to the invention in that the box-type container is united in a common housing, with a feeding chamber and with an air-conditioning chamber containing an air-conditioning means, wherein at least the front wall of the feeding chamber is made of transparent material and openings are provided therein for connecting manipulation aids, such as gloves, a gas-tightly closeable feed opening is provided in a side wall of the feeding chamber, and the air-conditioning means comprises a sterile filter for keeping sterile the intake air to be conducted through the box-type container and the feeding chamber, as well as a further sterile filter for filtering the offstreaming exhaust air, (which two sterile filters are connected with each other via a gas duct provided in the air-conditioning chamber and in which a first shut-off organ, a refrigerating unit, a fan and a heating unit are incorporated.

By means of such an arrangement, several operation steps—i.e., sterile growing of the microorganisms and inducing the formation of permanent forms by controllable environmental conditions, drying of the permanent forms and sterile harvesting—may be performed without high acquisition costs in an uncomplicated manner and under constantly sterile conditions. On account of the transparent front wall, the spore formation may be readily observed.

As the transparent material for the front wall of the feeding chamber, plexiglass in an aluminum frame may, for instance, be used, the front wall suitably being designed to be foldable upwards in its entirety. This design is very favorable primarily with a view to cleaning to be carried out from time to time, since the interior is directly accessible.

In the openings of the front wall, manipulation aids are fastened in an air-tightly closing manner, gloves of Neopren having proved particularly suitable.

Small appliances required in each case may be introduced through the feed opening.

Preferably, the upper cover of the common housing includes connections for a hypodermic needle arrangement in the region of the box-type container and of the feeding chamber, and, if desired, also is made of transparent material like the front wall.

These connections contain an optionally multi-layer septum of elastic material, for instance, silicon rubber. Sterile cannulas may be pierced through the septum without unsterile external air getting into the housing interior. The cannulas may be connected to syringe bodies or to a duct via a cone, thus enabling the supply of sterilized liquid or gaseous media into the housing interior.

According to a preferred embodiment, a bench provided with openings and pivotable about a horizontal axis is arranged below and in front of the box-type container, a space being provided therebelow for retaining articles.

Such articles may comprise equipment pieces temporarily not required, or possibly incurring waste impeding further operation. The articles may be conveyed into the space available therebelow without much work in a simple way by lifting the bench as far as into an approximately perpendicular position. The air circulating through the box-type container, through the feeding chamber and through the space for retaining articles may stream through the openings in the bench without impediment.

According to a further advantageous embodiment, a connection to a permanent spore-form harvesting device is disposed on the lower side of the feeding chamber, which harvesting device, in particular, is designed as a cyclone, from whose lateral connection socket a flexible tube leads to the connection provided on the lower side of the feeding chamber, whose central connection socket is connected, via a filter, to the suction side of a fan, and whose exhaust pipe is gas-tightly inserted in a collecting flask.

In this case, a suction pipe is kept in the feeding chamber, which pipe is connected with the connection provided on the lower side of the feeding chamber also via a flexible suction tube.

In order to adjust the desired humidity of the air circulating in the arrangement according to the invention, the cooling performance of the refrigerating unit and/or the residence time in the refrigerating unit, which, for instance, may be comprised of an air-cooled refrigerating compressor and a refrigerating register, is controlled. In order to prevent the formation of ice in the refrigerating register, the temperature of the coolant must be downwardly limited to about 0° C.

Suitably, the refrigerating unit is connected, via a second shut-off organ, with a condensate trap and, electrically, with a humidity controlling means, whose probe is incorporated in that section of the gas duct which extends between the heating unit and the intake-air sterile filter. The condensate incurring at the withdrawal of water from the air is collected in the condensate trap.

To precisely adjust the desired intake-air temperature, a temperature probe advantageously is provided in that section of the gas duct which extends between the heating unit and the intake-air sterile filter, which temperature probe is electrically connected with a temperature controller connected to the heating unit.

The heating unit, for instance, may be comprised of one or several electric heating rods. This type of heating is very robust, the heating performance being infinitely variable in the simplest manner.

In order to be able to admix determined portions of fresh air (intake air), i.e., to adjust the desired ratio of intake air and circulating air, and in order to enable the elimination of gaseous sterilizing agent, such as, e.g., ethylene oxide or formaldehyde, from the arrangement according to the invention, according to a further preferred modification, a fresh-air duct provided with a third shut-off organ enters into the gas duct between the refrigerating unit and the first shut-off organ, and a further duct branches off between the first shut-off organ and the exhaust-air sterile filter, which duct is consecutively equipped with a fourth shut-off organ, an auxiliary fan, an activated carbon filter and an air volumeter.

Through this additional duct, gas may be drawn off the arrangement by means of an auxiliary fan.

BRIEF DESCRIPTION OF THE DRAWINGS

The invention will now be explained in more detail with reference to the accompanying drawings, wherein:

FIG. 1 is a principle sketch of an embodiment of the arrangement according to the invention, from which the mode of operation is immediately apparent;

FIG. 6 illustrates in more detail a permanent-form harvesting means to be suitably combined with an arrangement according to the invention.

DESCRIPTION OF THE PREFERRED EMBODIMENTS

Figure 5:
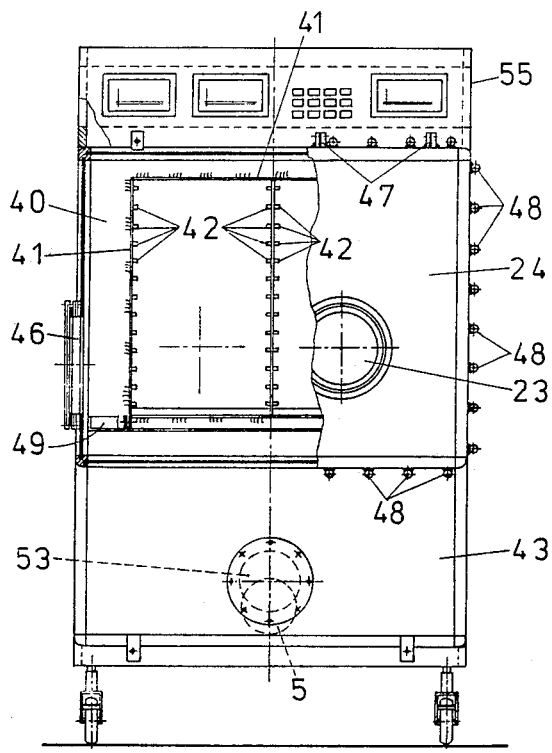
FIG. 5 is a view of the partially elevated arrangement according to FIG. 3 from the direction V.

In FIG. 1, a part of the common housing—i.e., that part which encloses a box-type container including trays 2 as well as the feeding chamber—is generally denoted by 1'. A sterile filter 3 is directly annexed to the box-type container not separately shown and containing the superposed trays 2 to keep the intake air sterile. The sterile filter 3, via a gas duct 4, is connected with a further sterile filter 5 for filtering the exhaust air. The direction of the gas mixture (in particular, air) streaming through the gas duct 4 is indicated by an arrow. A first shut-off organ 6, for instance, a flap or a valve, a refrigerating unit 7, a fan 8 and a heating unit 9 are incorporated in the gas duct 4.

The refrigerating unit 7 is connected to a receptacle 11 serving as a condensate trap via a second shut-off organ 10. In addition, there is an electric connection between the refrigerating unit 7 and a humidity controller 12, the latter being connected—again, in an electrically conducting manner—with and responsive to a pertaining humidity sensor 13 (not illustrated in detail) in the section of the gas duct 4 that extends between the heating unit 9 and the intake-air sterile filter 3. In the same section of the gas duct 4, a temperature sensor 14 (not illustrated in detail, either), furthermore, is provided, which is operatively connected with a temperature controller 15. The temperature controller 15 is operatively connected via electrical connection also to the heating unit 9.

Between the first shut-off organ 6 and the cooling unit 7, a fresh-air (intake-air) duct 17 equipped with a third shut-off organ 16 enters into the gas duct 4, a (exhaust gas) duct 18 branching off the gas duct 4 between the exhaust-air sterile filter 5 and the first shut-off organ 6, in which duct a fourth shut-off organ 19, an auxiliary fan 20, an activated carbon filter 21 and an air volumeter 22 are consecutively installed.

Figure 2:
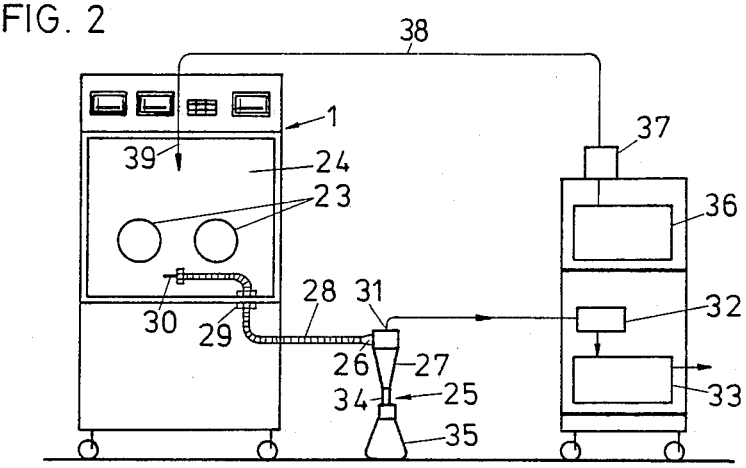
FIG. 2—also schematically—illustrates an arrangement according to the invention, with a harvesting means, a sterilizer for culture medium (agar) and a dosing pump for the liquid sterilized culture medium being attached thereto.

From FIG. 2, the front view of a movable arrangement 1 according to the invention is apparent, which includes two circular openings 23 for the connection of manipulation aids in the transparent front wall 24 of the feeding chamber. Above the front wall 24, which forms part of the common housing, a console may be seen, on which the graduations of measuring instruments as well as control buttons for adjusting the climatic conditions in the interior of the arrangement according to the invention are arranged.

A permanent-form harvesting means is generally denoted by 25, wherein a lateral connection socket 26 of a cyclone 27 made, for instance, of special steel is connected with a connection 29 provided on the bottom wall of the feeding chamber, by means of a flexible tube 28. Within the feeding chamber, a flexible tube leads on from the air-tight connection 29, ending in a suction pipe 30. The central connection socket 31 of the cyclone 27 is connected to the suction side of a further fan 33 via a filter 32, in which remaining spores not separated in the cyclone 27 are retained. The discharge pipe 34 of the cyclone 27 is gas-tightly inserted in a collecting flask 35 for permanent forms.

Hot liquid culture medium from a sterilizer 36 may be introduced under sterile conditions through the upper cover of the common housing by means of a dosing pump 37—for instance, a squeezed tube pump—via a duct 38 and a hypodermic needle 39 illustrated just schematically.

It is suitable to place the arrangement according to the invention, together with the auxiliary components described, in a thermostated room, with the air temperature of the thermostated room always having to be adjusted slightly higher than the temperature prevailing within the arrangement according to the invention in order to avoid vapors condensating at the walls of the common housing.

At the beginning of the growth cycle, the box-type container is filled with pre-sterilized trays 2, the necessary appliances being introduced into the feeding chamber.

Thereupon, the interior of the arrangement, except for the air-conditioning chamber, is filled with formaldehyde gas by evaporation and is kept for several hours until sterilization has been completed. Ethylene oxide is less suited for sterilization due to an elevated risk of explosion and the high human toxicity of this gas. Then, the first shut-off organ 6 is closed, the third and the fourth shut-off organs 16, 19 are opened, and the fan 8 as well as the auxiliary fan 20 are switched on. The formaldehyde vapors are sucked off and are condensed in the activated carbon filter 21. Then, the air-conditioning means is switched on, the temperature, the humidity of the air and the ratio fresh air/circulating air are adjusted. To this end, the first shut-off organ 6 is reopened with the third and fourth shut-off organs 16, 19 still opened, and the desired fresh-air/circulating-air ratio to be determined by the air volumeter 22 is adjusted by controlling the number of revolutions of the auxiliary fan 20. In the meantime, the culture medium is prepared in the sterilizer 36 and is pumped in a sterile state into the individual trays 2 via a hypodermic needle 39 by means of the dosing pump 37. When using a squeezed tube pump, the amount of culture medium to be added in each case suitably is adjusted upon previous calibration via the pumping time by means of a timer.

After solidification of the culture medium, an innoculation suspension of the microorganisms, or spores, is applied onto the trays 2 likewise by means of a dosing pump or a syringe according to the hypodermic needle technique, and is distributed, for instance, by means of a Drigalski spatula.

The growing time and the sporulation time as well as the growing conditions very strongly depend on the microorganism used. As the permanent forms have come into existence, the air humidity and the temperature of the circulating air are changed over to drying conditions.

After adequate drying, the spores formed are sucked off by the harvesting means 25 and, thus, are transferred into the collecting flask 35 suitably made of glass. Thereupon, the harvested trays are removed from the arrangement, the latter being cleaned and prepared for a new growth cycle.

Figure 3:
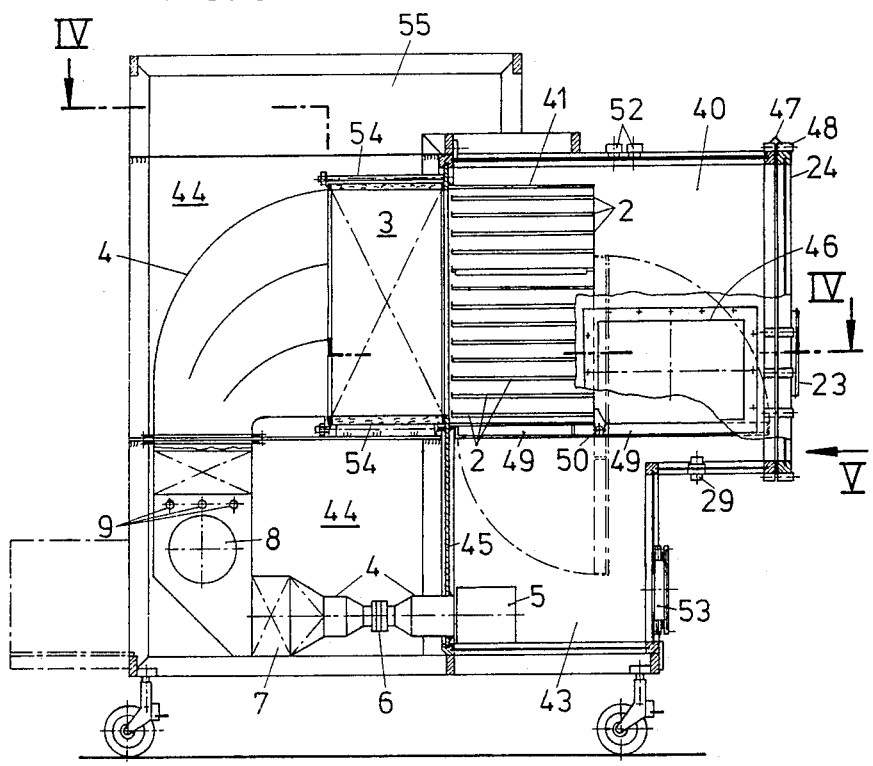
FIG. 3 represents a special design of a movable arrangement according to the invention, largely in section.
Figure 4:
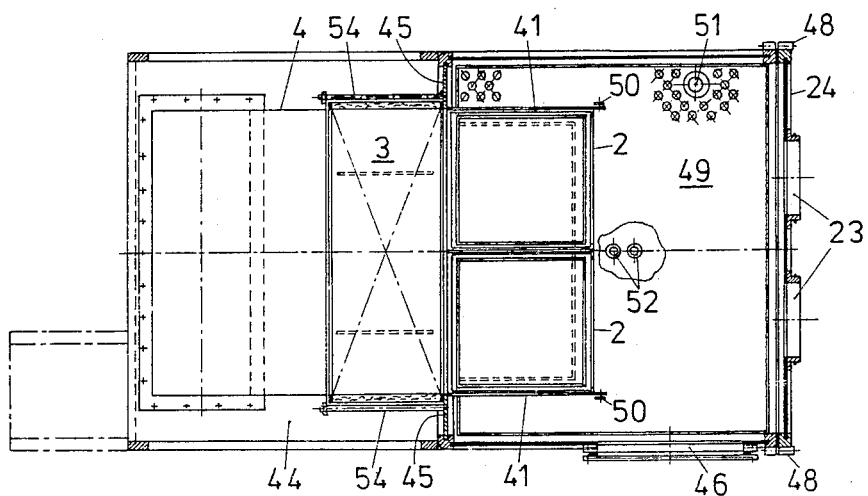
FIG. 4 is a sectional view of the arrangement according to FIG. 3 along line IV—IV of FIG. 3.

With the special embodiment of an arrangement according to the invention as shown in FIGS. 3 to 5, a box-type container 41 is open towards the feeding chamber 40. It contains rails 42 for pushing in the trays 2 receiving the culture medium. The front wall 24 of the feeding chamber 40, the upper cover of the common housing in the region of the box-type container 41 and in the region of the feeding chamber 40, the lower side of the feeding chamber 40, all the side walls of these arrangement compartments including all the limitation walls of the space 43 disposed therebelow are made of plexiglass panes, which are gas-tightly inserted in aluminum sections, the latter constituting the edges of the common housing in the this region. The air-conditioning chamber 44 is annexed to the common rear wall 45 of the box-type container 41 and of the space 43. The walls of the air-conditioning chamber 44 are not made of transparent material.

In the left side wall of the feeding chamber 40, seen from the front wall 24, a rectangular feed opening 46 is arranged to be closeable in a gas-tight manner. The front wall 24 may be folded upwardly about hinges 47 in its entirety. In the closed state, it is pressed on a peripheral seal by means of fastening elements provided along its rim, for instance by screw connections 48. In the front wall 24, two circular openings 23 for the air-tight connection of gloves (not illustrated) are provided in order to be able to carry out necessary operations in the feeding chamber 40 or in the box-type container 41 by maintaining sterile conditions.

A bench 49 including openings is provided directly below and in front of the container 41, which bench is recessed in the form of a U below the box-type container 41 and is pivotably mounted in two bearings 50. The bench turned into the vertical position is entered in FIG. 3 in dot-and-dash lines. In this position of the bench 49, even the space 43 arranged therebelow, which, i.a., serves to retain equipment pieces not required, is accessible from the feeding chamber 40.

On the lower side of the feeding chamber 40, there is a connection 29 to the permanent-form harvesting means described already in connection with FIG. 2. A recess 51 is provided in the bench 49 to pass therethrough the flexible tube leading from the connection 29 to a suction pipe 30 (FIG. 2).

Furthermore, two connections 52 for pricking needle technique are provided in the upper cover of the common housing.

In order to facilitate the removal of waste from the space 43, a removal opening 53 also hermetically sealable is provided in the front wall of this space. In the bottom region of the space 43, a section of the gas duct 4 is sealedly led into the space 43 through the common rear wall 45. The end of the gas duct is connected to an exhaust-air sterile filter 5. An intake-gas sterile filter 3 communicates with the other end of the gas duct 4. The sterile filter 3 is disposed in the air-conditioning chamber 44 and is sealingly connected with the rim of a corresponding cutout in the rear wall 45 via its frame 54. The sterile air, which is fed directly behind the trays 2 over a comparatively large cross-sectional area of the sterile filter 3 streams over all the trays in a laminar manner, thus creating readily controllable climatic conditions.

In the gas duct 4, a first shut-off organ 6, a refrigerating unit 7, a fan 8 and a heating unit 9 including three electric heating rods are consecutively installed after the exhaust-air sterile filter 5, seen in the flow direction of the air. The functions of these arrangement parts have already been pointed out in detail in connection with FIGS. 1 and 2.

The necessary electric and electronic equipment, such as the measuring and controlling appliances described, are housed in a console room 55, which may be considered as part of the air-conditioning chamber 44. The indicator graduations of the measuring instruments are provided on the external side of the front wall of the console room 55. The electric appliances as well as the electric conduits are not illustrated in FIGS. 3 to 5.

The permanent-form harvesting means 25 according to FIG. 2 is illustrated in an enlarged and partially sectioned manner in FIG. 6.

The discharge pipe 34 of the cyclone 27 is gas-tightly inserted in the collecting flask 35 by means of a pierced through plug 56 of elastic material. A stream of air loaded with spores tangentially gets into the cyclone through the lateral connection socket 26. In doing so, the major portion of the spores borne by the stream of air is separated, falling through the discharge pipe 34 into the collecting flask 35. The air, which contains but residual spores, leaves the cyclone 27 through the central connection socket 31.

With an approximate volume of the arrangement (without air-conditioning chamber) of 0.9 $m^3$, it has proved favorable to design the following components in terms of performance as follows:

Fan 8: variable number of revolutions, blower output 0 to 50 $m^3$ gas (air)/h

Auxiliary fan 20: variable number of revolutions, blower output 0 to 20 $m^3$ air/h Refrigerating unit 7 (refrigerating compressor and refrigerating register):
20 $m^3$ air/h
33° C. to 4° C. power input about 700 W Heating unit 9 (three electric heating rods): power approx. 500 W, infinitely variable Air volumeter 22: suited to measure exhaust-gas and fresh-air (intake-air) amounts from 0.5 to 5 $m^3$/h.

What we claim is:

1. In an arrangement for growing permanent forms of microorganisms and for harvesting permanent forms on the surface of a culture medium, of the type including a box-type tray container and a plurality of trays arranged in said container to receive said culture medium, the improvement comprising:

a common housing enclosing a feeding chamber and air conditioning means, said feeding chamber containing said tray container, said feeding chamber having a transparent front wall provided with openings for manipulation aids to be connected thereto, said feeding chamber having a side wall provided with a gas-tight closable feed opening, said feeding chamber including air inlet and air outlet, a first sterile filter positioned at said air inlet for filtering air to be conducted through said feeding chamber, and a second sterile filter positioned at said air outlet for filtering air exhausted from said feeding chamber, duct means within said common housing for joining said air inlet and said air outlet directly to permit flow of air from said air outlet to said air inlet, said duct means including in consecutive sequence in direction from said air outlet to said air inlet, a first shut-off means for controlling said air through said air outlet, refrigerating means for adjusting humidity of said air, a fan for circulating said air and heating means for heating said air.

2. An arrangement as set forth in claim 1, further comprising means for trapping condensate from said refrigerating means, said means for trapping condensate comprising a receptacle for receiving condensate, means for conducting said condensate from said refrigerating means to said receptacle, and a second shut-off means for controlling the flow of condensate from said refrigeration means to said receptacle; and humidity sensing means in the section of said gas duct between said heating means and said first sterile filter, and means for controlling the cooling performance of the refrigeration means and/or the residence time therein, said means being responsive to said humidity sensing means.

3. An arrangement as set forth in claim 1, wherein said manipulation aids comprise gloves.

4. An arrangement as set forth in claim 1, wherein said front wall of said feeding chamber is adapted to be folded upwards in its entirety.

5. An arrangement as set forth in claim 1, wherein said common housing has an upper cover and said upper cover includes hypodermic needle connections in the region of said box-type tray container and of said feeding chamber.

6. An arrangement as set forth in claim 5, wherein said upper cover is transparent.

7. An arrangement as set forth in claim 1, further comprising a bench arranged below and in front of said box-type tray container so as to be pivotable about a horizontal axis and provided with openings, and a space provided below said bench for retaining articles.

8. An arrangement as set forth in claim 1, wherein said feeding chamber has a bottom wall provided with connecting means to a permanent-form microorganism harvesting means, a suction pipe within said feeding chamber for withdrawing spore loaded air therefrom and a suction tube connecting said suction pipe with said connecting means.

9. An arrangement as set forth in claim 8, further comprising a permanent-form micoorganism harvesting means including cyclone means provided with a lateral connection socket, a central connection socket and a discharge pipe, a flexible tube leading from said lateral connection socket to said connecting means provided on said bottom wall of said feeding chamber, a filtering means, and a fan, said fan communicating on its suction side with and providing suction to said central connection socket via said filtering means, and a collecting flask receiving said discharge pipe in a gas-tight manner.

10. An arrangement as set forth in claim 1, further comprising air temperature sensing means provided in the section of said gas duct between said heating means and said first sterile filter, and air temperature controlling means operatively connected to said heating means and electrically communicating with and responsive to said temperature sensing means.

11. An arrangement as set forth in claim 1, further comprising a fresh-air intake duct entering into said gas duct between said refrigerating means and said first shut-off means and provided with a third shut-off means for controlling the fresh-air intake, and an exhaust duct branching off between said first shut-off means and said second sterile filter and having a fourth shut-off means for controlling the flow of exhaust air, an auxiliary fan for exhausting the air, an activated carbon filter and an air volumeter for measuring the exhaust air situated therein in consecutive sequence.

* * * * *